(12) United States Patent
Bredno et al.

(10) Patent No.: US 8,908,939 B2
(45) Date of Patent: Dec. 9, 2014

(54) PERFUSION IMAGING

(75) Inventors: Joerg Bredno, San Francisco, CA (US); Max Wintermark, San Francisco, CA (US)

(73) Assignee: Koninklijke Philips N.V., Eindhoven (NL)

( * ) Notice: Subject to any disclaimer, the term of this patent is extended or adjusted under 35 U.S.C. 154(b) by 483 days.

(21) Appl. No.: 13/062,227

(22) PCT Filed: Sep. 10, 2009

(86) PCT No.: PCT/IB2009/053964
§ 371 (c)(1),
(2), (4) Date: Mar. 4, 2011

(87) PCT Pub. No.: WO2010/038161
PCT Pub. Date: Apr. 8, 2010

(65) Prior Publication Data
US 2011/0211742 A1    Sep. 1, 2011

Related U.S. Application Data

(60) Provisional application No. 61/101,160, filed on Sep. 30, 2008.

(51) Int. Cl.
*G06K 9/00* (2006.01)
*A61B 6/00* (2006.01)
*G06F 19/00* (2011.01)
*A61B 6/03* (2006.01)

(52) U.S. Cl.
CPC ............... *A61B 6/504* (2013.01); *A61B 6/481* (2013.01); *G06F 19/3437* (2013.01); *A61B 6/507* (2013.01); *A61B 6/032* (2013.01); *G06F 19/321* (2013.01); *G06F 19/3406* (2013.01)
USPC ........................................................ 382/128

(58) Field of Classification Search
USPC .......................... 382/128, 131; 128/922, 923; 250/363.04; 378/4, 21, 23
See application file for complete search history.

(56) References Cited

U.S. PATENT DOCUMENTS

| | | | | |
|---|---|---|---|---|
| 5,494,655 | A  * | 2/1996 | Rocklage et al. | 424/9.36 |
| 5,685,305 | A  * | 11/1997 | Moonen et al. | 600/419 |
| 6,295,465 | B1 * | 9/2001 | Simonetti | 600/413 |
| 6,745,066 | B1 * | 6/2004 | Lin et al. | 600/425 |
| 7,218,702 | B2 | 5/2007 | Mistretta et al. | |
| 2002/0161296 | A1 * | 10/2002 | Kuth et al. | 600/420 |
| 2003/0097076 | A1 | 5/2003 | Nambu et al. | |
| 2006/0004279 | A1 * | 1/2006 | Ikeda et al. | 600/411 |
| 2006/0083687 | A1 * | 4/2006 | Yang | 424/9.3 |
| 2006/0155185 | A1 * | 7/2006 | Breeuwer | 600/407 |

(Continued)

FOREIGN PATENT DOCUMENTS

| | | | |
|---|---|---|---|
| EP | 1790289 | A2 | 5/2007 |
| WO | 03046797 | A2 | 6/2003 |
| WO | 2006067201 | A2 | 6/2006 |

OTHER PUBLICATIONS

Miles, K. A., et al.; Perfusion CT: a worthwhile enhancement?; 2003; The British Journal of Radiology; 76:220-231.

*Primary Examiner* — Shervin Nakhjavan

(57) ABSTRACT

A system includes a perfusion information determiner (124) that determines perfusion information based on a combination of pre-perfusion scan image data and perfusion scan image data.

28 Claims, 2 Drawing Sheets

(56) References Cited

U.S. PATENT DOCUMENTS

| | | |
|---|---|---|
| 2006/0184002 A1* | 8/2006 | Yarnykh et al. ............... 600/410 |
| 2006/0215889 A1* | 9/2006 | Omi et al. .................... 382/128 |
| 2007/0009080 A1* | 1/2007 | Mistretta .......................... 378/4 |
| 2008/0262344 A1* | 10/2008 | Brummett .................... 600/426 |
| 2008/0292049 A1* | 11/2008 | Camus et al. ................... 378/21 |
| 2009/0036784 A1* | 2/2009 | Lee ............................... 600/481 |

* cited by examiner

PERFUSION IMAGING

CROSS REFERENCE TO RELATED APPLICATIONS

This application claims the benefit of U.S. provisional application Ser. No. 61/101,160 filed Sep. 30, 2008, which is incorporated herein by reference.

The following generally relates to perfusion imaging, and finds particular application to computed tomography perfusion (CTP). However, it is also amenable to other medical imaging applications and to non-medical imaging applications.

Computed tomography perfusion (CTP) is a medical imaging technique that is used to facilitate diagnosing patients with mal-perfusion of the brain like stroke patients. A CTP scan shows the transit of an administered contrast agent through brain tissue along with the cerebral blood supply. To ensure that this transit is well captured in a scan with limited duration, a planning phase has been used. This phase includes administering an intravenous contrast agent bolus to a patient that is about to be scanned. The patient's carotid arteries are then dynamically scanned until the arrival of the contrast agent at the carotid arteries is observed in the resulting images. Traditionally, such a scan covered a region of interest that included both carotid bifurcations and approximately one (1) centimeter (cm) above and below this plane. The amount of time between the administration of the contrast agent and the time when the contrast agent reaches the carotid arteries is manually determined and provides information that is used to determine the CTP scan start time, relative to the administration of a contrast agent.

For the CTP scan, an intravenous contrast agent bolus is administered. Based on the above-noted timing and a prior knowledge regarding arterial blood flow, the CTP scan is dynamically performed after a time delay from the administration of the contrast agent in an attempt to capture the interval in which the contrast agent arrives at and washes out of the tissue of interest in the scan field of view. This region traditionally has included brain areas perfused by the mid-cerebral and anterior-cerebral arteries. The contrast agent causes the x-ray density of the brain to temporarily increase as the contrast agent flows through the vascular structure of the brain. The scan includes acquiring data that covers multiple different time intervals so that the contrast agent is captured and traced as the contrast agent washes in and washes out through such vascular structures. The CTP scan has alternatively been performed without first performing the planning pre-scan. However, this carries the risk of not completely imaging the first pass of contrast agent through the tissue. In this undesired case, the CTP scan with its associated X-ray dose burden to the patient is not suitable for a subsequent quantitative assessment of the brain perfusion.

The CTP data can be used to determine time-attenuation curves showing contrast agent concentration for a particular region in the scan field of view over time. Such curves have been determined from parenchymal voxels and feeding arteries, which generally provide good reference data. From these curves, the perfusion status of the imaged tissue can be determined. The resulting data can be used to identify ischemic tissue and/or differentiate between irreversibly damaged tissue (necrotic tissue, or the ischemic core) and potentially reversibly damaged tissue (at-risk tissue, or the ischemic penumbra), for example, in stroke patients. Independently, a static CT angiography (CTA) scan is often acquired to assess the status of the endovascular lumen of major vessels. With a static CTA, a contrast agent is administered and a larger coverage scan, e.g. using a spiral or helical scan is performed in order to capture a larger portion of the arterial system supplying blood to the brain.

Conventionally, CTP analysis is used to determine the perfusion status of brain tissue based on the observations of contrast agent dynamics in the scan field of view. However, cerebral perfusion deficits generally cannot be interpreted as a disease of the brain alone, but, as a systemic disease, it is influenced by different malfunctions or lesions in the vascular system. As such, conventional analysis may lead to misinterpretation, for example, in cases where the perfusion deficit is apparent in the image data, but caused in arteries outside the image data. For example, a stenosis of a carotid artery may mimic a mal-perfusion such as a hypo-perfusion of the corresponding cerebral hemisphere. As such, without additional information, slow blood flow and late contrast arrival may be interpreted as result of an obstruction in the imaged arteries (the mid- and anterior-cerebral arteries) when the obstruction is a carotid stenosis.

Aspects of the present application address the above-referenced matters and others.

According to one aspect, a system includes a perfusion information determiner that determines perfusion information based on a combination of pre-perfusion scan image data and perfusion scan image data.

According to another aspect, a computer readable storage medium containing instructions which, when executed by a computer, cause the computer to perform the steps of: determining one or more contrast time-attenuation curves based on one or more of pre-perfusion scan image data and perfusion scan image data; deriving flow data for arteries not in but affecting perfusion of tissue in the perfusion scan image data based on the one or more contrast time-attenuation curves and an anatomical model; determining one or more flow parameters based on the one or more contrast time-attenuation curves and the derived perfusion data; and determining perfusion information based on the one or more perfusion parameters.

According to another aspect, a method includes determining perfusion information about scanned tissue of interest based on a combination of pre-perfusion scan image data and perfusion scan image data.

The invention may take form in various components and arrangements of components, and in various steps and arrangements of steps. The drawings are only for purposes of illustrating the preferred embodiments and are not to be construed as limiting the invention.

Figure 1:
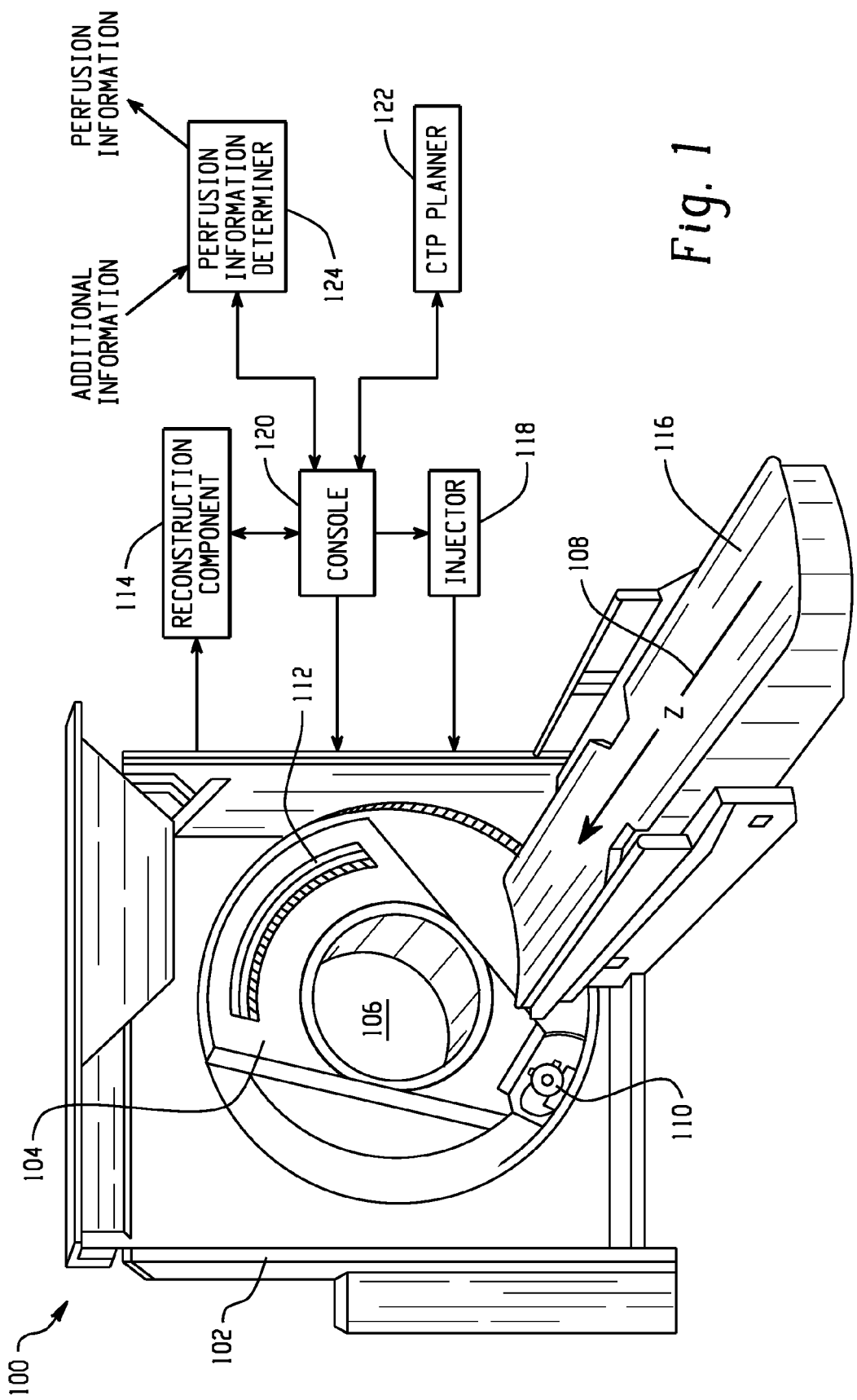
FIG. 1 illustrates a perfusion information determiner in connection with an imaging system.

Initially referring to FIG. 1, a computed tomography (CT) scanner 100 includes a stationary gantry 102 and a rotating gantry 104, which is rotatably supported by the stationary gantry 102. The rotating gantry 104 rotates around an examination region 106 about a longitudinal or z-axis 108.

A radiation source 110, such as an x-ray tube, is supported by and rotates with the rotating gantry 104 around the examination region 106. The radiation source 110 emits generally fan, wedge, or cone shaped radiation that traverses the examination region 106.

A radiation sensitive detector array 112 detects photons emitted by the radiation source 110 that traverse the examination region 106 and generates projection data indicative of the detected radiation. The illustrated radiation sensitive detector array 112 includes one or more rows of radiation sensitive photosensors that extend in a z-axis or longitudinal direction, and one or more columns of radiation sensitive photo sensors that extend in a traverse direction.

A reconstructor 114 reconstructs the projection data from the detectors to generate volumetric image data indicative of the examination region 106, including the interior anatomy, such as a portion of the vascular system, of a patient disposed in the examination region 106.

A patient support 116, such as a couch, supports a patient in the examination region 106. The patient support 116 is movable along the z-axis 108 in coordination with the rotation of the rotating gantry 104 to facilitate helical, axial, or other desired scanning trajectories.

An injector 118 is configured to inject or administer a material such as one or more contrast agents to an object or subject, such as a human or animal patient, being scanned. The contrast agent may include a single contrast material or multiple contrast materials. A contrast agent can alternatively be manually administered by a clinician or the like.

A general purpose computing system serves as an operator console 120, which includes human readable output devices such as a display and/or printer and input devices such as a keyboard and/or mouse. Software resident on the console 120 allows the operator to control the operation of the system 100, for example, by allowing the operator to select a scan protocol such as a CTP protocol, initiate and terminate scanning, view and/or manipulate the volumetric image data, and/or otherwise interact with the system 100.

In one instance, the scanner 100 is used to repeatedly acquire data used to determine perfusion information about a subject. This may include performing a pre-perfusion scan to determine timing information for a perfusion scan of tissue of interest. For the pre-perfusion scan, a contrast agent is administered to the subject, and a dynamic scan consisting of multiple acquisitions of one region of interest is performed to determine when the contrast agent arrives at reference vessels or tissue, which typically is located upstream from the tissue of interest in that the contrast agent arrives at the reference vessel or tissue prior to arriving at the tissue of interest. Generally, the pre-perfusion scan coverage does not include the tissue of interest.

The pre-perfusion scan image data is provided to a CTP planner 122, which determines the amount of time it takes for the contrast agent to arrive at the reference vessel or tissue. Based at least in part on this information, the CTP planner 122 determines a perfusion scan start time relative to the administration of a contrast agent. Other information, such as information about perfusion in the reference tissue, the tissue of interest and/or tissue affecting perfusion in the tissue of interest is also to be used to determine the perfusion scan start time.

Like the pre-perfusion scan, a contrast agent is administered to the subject, and a dynamic scan is performed, but based on the perfusion scan start time determined from the pre-perfusion image data. Generally, the perfusion scan coverage does not include the reference vessel or tissue. That is, generally the scan coverage of the perfusion scan and the scan coverage of the pre-perfusion scan do not overlap or cover contiguous regions. As such, connecting vessels or tissue that may affect perfusion in the tissue of interest is absent from this image data.

A perfusion information determiner 124 determines perfusion information for the tissue of interest and optionally tissue affecting perfusion through the tissue of interest at least based on the pre-perfusion scan and perfusion scan image data. Other information, such as information obtained by another imaging procedure, laboratory test, subject medical history, anatomical models, and/or otherwise can additionally be used to determine the perfusion information.

As described in greater detail below, the pre- and perfusion scan image data can be used to derive perfusion data for connecting vessels or tissue between the reference tissue and the tissue of interest. In one instance, the combination of this derived data and perfusion data determined from the pre- and/or perfusion scan provides information used to discriminate between perfusion deficits in the tissue of interest and perfusion deficits in the reference, connecting and/or other vessels or tissue. As such, the cause for a perfusion deficit apparent in, but located outside of the tissue of interest can be correctly identified and mapped to the corresponding tissue.

A non-limiting example of a suitable tissue of interest includes arteries supplying blood to the brain. In this instance, the pre-scan includes administering a contrast agent, such as an iodated contrast agent bolus or other contrast agent, and subsequently dynamically scanning the subject's arteries, such as both carotid arteries, including the carotid bifurcations and surrounding tissue. In other instance, tissue including the same and/or different tissue is scanned.

As noted above, the resulting image data is fed to the CTP planner 122, which determines a perfusion scan start time based at least in part on this information. For the cerebral CTP, a contrast agent is administered, and the scan is performed based at least in part on the determined scan start time. In one instance, the resulting image data includes information indicative of blood flow through the mid-cerebral arteries, the anterior-cerebral arteries, tissue perfused by these arteries and/or other vascular tissue.

Both the pre-perfusion scan image data, which in this example is indicative of the carotid bifurcations and surrounding tissue, and the perfusion image data, which in this example is indicative of the mid-cerebral and anterior-cerebral arteries, are provided to the perfusion information determiner 124. Other information such as an anatomical model and/or other vascular related data can also be provided to the perfusion information determiner 124.

From this data, the perfusion information determiner 124 can derive blood flow and perfusion data for vascular tissue not in the pre- or perfusion scan image data. In one instance, this includes deriving blood flow data for the internal carotid arteries, the anterior communicating arteries, other vascular tissue between and/or affecting perfusion in the carotid bifurcations, surrounding tissue, mid-cerebral and anterior-cerebral arteries, and/or other vascular tissue.

Based on the pre-scan, perfusion scan, and derived data, the perfusion information determiner 124 can identify and discriminate between perfusion deficits in the carotid arteries, the internal carotid arteries, the anterior communicating arteries, the mid-cerebral arteries, the anterior-cerebral arteries, and/or other vascular tissue. As such, perfusion deficits apparent in the perfusion image data, but caused in other vascular tissue can be mapped to the correct tissue.

The perfusion information determiner 124 may also additionally or alternatively use various other information. For example, the perfusion information determiner 124 may use information acquired by another CT scanner and/or other imaging modality such as magnetic resonance (MR), ultrasound (US), single photon emission computed tomography (SPECT), positron emission tomography (PET), etc. Such information may include, for example, perfusion related information such CTA, MRA, DSA, and/or other image data. The perfusion information determiner 124 may also generate and/or employ perfusion maps such as cerebral blood flow (CBF), cerebral blood volume (CBV), mean transit time (MTT), and time to peak (TTP) perfusion maps, and/or summary maps that show the results of an automated classification of perfusion status. Other information that can be used by the perfusion information determiner 124 includes pathological information, patient medical history, physiological parameters (e.g., vital signs), etc.

Figure 2:
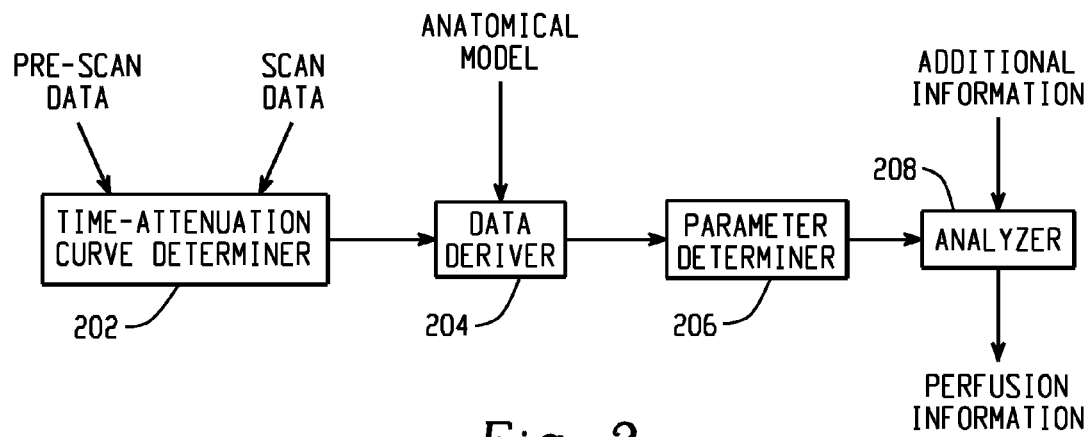
FIG. 2 illustrates an example perfusion information determiner

FIG. 2 illustrates an example embodiment of the perfusion information determiner 124. In the illustrated embodiment, the perfusion information determiner 124 includes a time-attenuation curve determiner 202, a data deriver 204, a parameter determiner 206, and an analyzer 208.

The time-attenuation curve determiner 202 generates time-attenuation curves based on pre-perfusion scan data, the perfusion scan data, and/or other data. In one instance, this may include indentifying a region of interest in vascular tissue (feeding arteries and/or other tissue) in the image data from for parenchymal voxels, and generating a time-attenuation curve of contrast density (e.g., in Hounsfield or other units) as a function of time for the region of interest.

It is to be appreciated that the region of interest may be identified automatically via executing computer readable instructions and/or manually by a clinician via a graphical and/or command line user interface. In addition, in another embodiment the time-attenuation curve determiner 202 may be omitted, and the time-attenuation curves may be generated by another component and provided to the perfusion information determiner 124.

The data deriver 204 derives or estimates blood flow and perfusion data based on the time-attenuation curves, anatomical models, and/or the pre-perfusion and perfusion image data. As noted above, the pre-perfusion scan image data may include data indicative of the carotid bifurcation and some surrounding tissue and the perfusion scan image data may include data indicative of the mid-cerebral arteries and the anterior-cerebral arteries. The data deriver 204 can derive additional blood flow data for the vessels therebetween, including, but not limited to the internal carotid arteries, the anterior communicating arteries, and/or other vascular tissue. Such data may connect the perfusion data for the imaged tissue in two different fields of view like the pre-scan and the brain perfusion scan in time and space for a joint analysis.

The parameter determiner 206 determines various parameters from the attenuation curves. Examples of suitable parameters include, but are not limited to contrast agent arrival time, peak contrast agent arrival time, contrast agent mean transit time in one or more vessel or perfused tissue, etc. Such information can be extracted out of or derived from the time-attenuation curves. Other information such as the pre-perfusion and/or perfusion image data and/or other data may also be used to derive these parameters.

The analyzer 208 analyzes the image data, the time-attenuation curves, and/or the parameters, and determines perfusion information therefrom. Such information may be related to the vascular tissue in the perfusion scan, the vascular tissue in the pre-perfusion scan, and/or the vascular tissue connecting and/or affecting perfusion in the vascular tissue in the perfusion scan and pre-perfusion scan.

The following provides various non-limiting examples of perfusion information that can be generated by the analyzer 208. In one instance, the analyzer 208, based on such information, determines differences in contrast agent arrival and/or mean transit time between the right and left carotid bifurcations, which may indicate a hemodynamically relevant stenosis in one of the common carotids.

In another instance, the analyzer 208 may compare the time-attenuation curves at both carotid bifurcations and the dominantly fed right and left mid-cerebral arteries visible in the perfusion scan image data, which may represent the flow through the internal carotid arteries and the differences in flow. Imbalanced inflow caused by a hemodynamically significant stenosis in one of the internal carotids can be detected by the comparison of two acquisitions with similar contrast agent injections and a right and left side that are nearly symmetric for physiological flow conditions.

In another instance, the analyzer 208 may compare the time-attenuation-curves in the anterior-cerebral artery to those at the carotid bifurcations, which may indicate the status of the dominant anterior communicating circulation. When the time difference between the contrast agent arrival in the right and left carotid is greater than the difference observed for the mid-cerebral arteries, compensating anterior communicating blood flow can be assessed.

The analyzer 208 may also compare the arterial time-attenuation-curves in carotids and the mid-cerebral arteries and quantify the imbalance of contrast agent inflow into the perfused brain tissue. This information may be used to compensate for a bias of perfusion measurements that is reported for some conventional brain perfusion analyses.

If different amounts of contrast agent are injected for the pre-perfusion and the perfusion scans, a deconvolution of the injection pulse of known duration can be applied for correction prior to any comparison.

When CTA image data is also provided to the analyzer 208, the analyzer 208 can use the geometry of vessels seen in the CTA to adjust the anatomical model that describes the vessels that connect the pre-scan and the brain perfusion scan from a general, physiologically normal geometry of connecting arteries to a patient-specific geometry. The analyzer can further use the information on transit times through the internal carotid arteries in connection with the analysis of diffuse stenoses observed on the static CTA scans.

The analyzer 208 may provide such information to the console 120, for example, to archive or display, and/or elsewhere such as to memory, a database, a server, a network, a picture archiving and communication systems (PACS), a hospital information system (HIS), radiology information system (RIS), a printer, a filmer, etc.

Although the pre-perfusion and perfusion image data in the above examples is acquired by the CT scanner 100, it is to be appreciated that such image data can additionally or alternatively be acquired by another imaging modality such as MR, US, SPECT, PET, etc.

Figure 3:
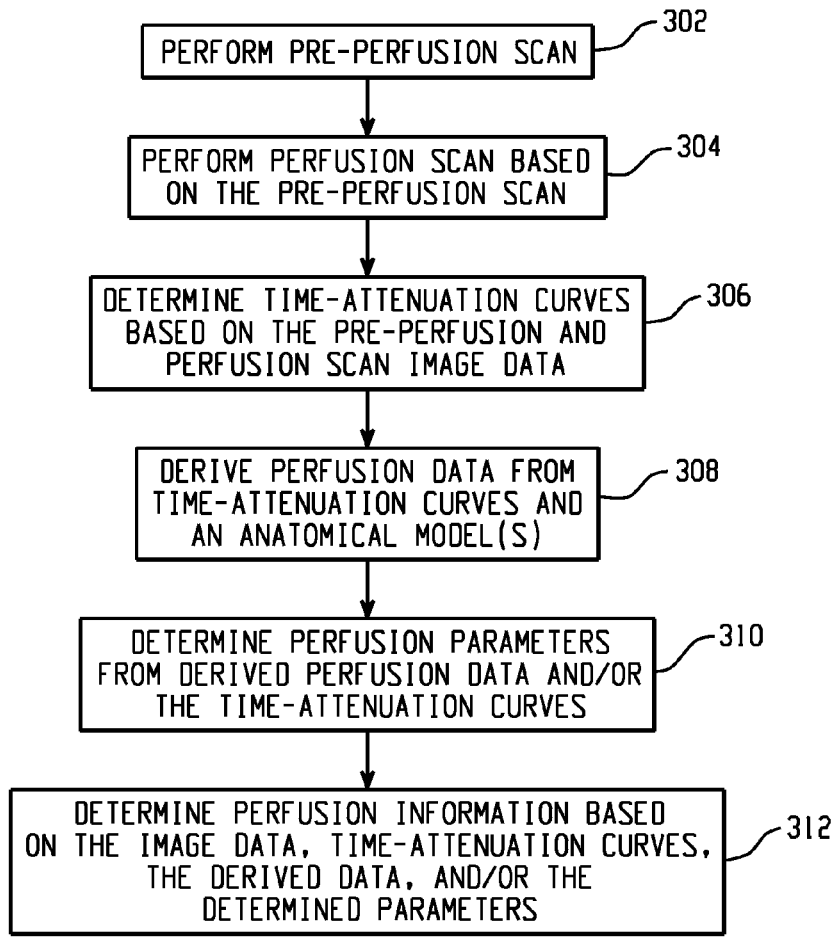
FIG. 3 illustrates a method for determining information.

Operation is now described in connection with FIG. 3.

At 302, a pre-perfusion scan is performed. As discussed above, for this scan a contrast agent is administered to a subject and a dynamic scan is performed to determine when the contrast agent arrives in predetermined reference tissue, such as the carotid bifurcations and some surrounding tissue.

At 304, a perfusion scan is performed based on the pre-perfusion scan image data. As noted above, this includes using the time it takes for the contrast agent to reach the reference tissues, as determined from the pre-perfusion scan image data, to determine when an administered contrast agent should reach tissue of interest, such as the mid-cerebral arteries and the anterior-cerebral arteries, and perfusion scanning should begin.

At 306, contrast time-attenuation curves are generated based on the pre-perfusion and perfusion scan image data. As discussed above, this may include determining contrast concentration via radiodensity for a region of interest over time.

At 308, perfusion data for tissue between and/or affecting perfusion in the tissue in the pre-perfusion and perfusion scan image data is derived from the time-attenuation curves and one or more anatomical models of such tissue. If a scan showing the geometry of the connecting arteries (e.g. a CTA scan) is available, then this scan can be used to adjust the anatomical model to a patient-specific model.

At 310, various perfusion parameters are determined from the image data, time-attenuation curves, and/or derived data. Such parameters may be indicative of contrast agent arrival time, peak contrast agent arrival time, contrast agent mean transit time in one or more vessels, contrast agent mean transit time in perfused tissue, and/or other information.

At 312, perfusion information for the vascular tissue in the pre-perfusion scan image data, the perfusion scan image data, and/or other vascular tissue is determined based on the image data, the time-attenuation curves, the determined parameters, and/or other information.

The above may be implemented by way of computer readable instructions, which when executed by a computer processor(s), cause the processor(s) to carry out the described acts. In such a case, the instructions are stored in a computer readable storage medium associated with or otherwise accessible to the relevant computer. The acts need not be performed concurrently with data acquisition.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

We claim:

1. A system, comprising:
   computer memory that stores pre-perfusion image data generated by repeatedly scanning, with a scanner, first vascular tissue of a subject, which feeds vascular tissue of interest of a subject that is upstream from the first vascular tissue, during a pre-perfusion contrast enhanced scan of the first vascular tissue, wherein the pre-perfusion image data does not include the vascular tissue of interest, and perfusion image data of the vascular tissue of interest generated by a perfusion scan of the vascular tissue of interest that is based on an imaging plan and that does include the first vascular tissue; and
   a computer processor that processes the pre-perfusion image data and determines an amount of time from an administration of a first contrast agent for the pre-perfusion contrast enhanced scan to arrival of the administered contrast agent at the first vascular tissue, creates an imaging plan for a perfusion scan of the vascular tissue of interest based on the amount of time so that the perfusion scan acquires data representing an arrival of an administered second contrast agent at the vascular tissue of interest, and that processes the pre-perfusion image data and the perfusion image data and determines first perfusion information for connecting vascular tissue, which vascularly connects the first vascular tissue and the vascular tissue of interest, based on the pre-perfusion scan image data and the perfusion image data.

2. The system of claim 1, the computer processor further processes the pre-perfusion image data and the perfusion image data and determines second perfusion information for the first vascular tissue from the pre-perfusion image data.

3. The system of claim 2, the computer processor further processes the pre-perfusion image data and the perfusion image data and determines third perfusion information for the vascular tissue of interest from the perfusion image data.

4. The system of claim 3, wherein the computer processor determines the first, the second and the third perfusion information by generating a first time-attenuation curve of contrast density for the first vascular tissue from the first perfusion image data; generating a second time-attenuation curve of contrast density for the vascular tissue of interest from the second perfusion image data; and deriving a third time-attenuation curve of contrast density for the connecting vascular tissue from the first time-attenuation curve and the second time-attenuation curve.

5. The system of claim 4, the computer processor further estimates first blood flow for the first vascular tissue based at least on the first time-attenuation curve; estimates second blood flow for the vascular tissue of interest based at least on the second time-attenuation curve; and derives third blood flow for the connecting vascular tissue based on the first blood flow estimate and the second blood flow estimate.

6. The system of claim 5, the computer processor further determines one or more of a first contrast agent arrival time, a first peak contrast agent arrival time, or a first contrast agent mean transit time for the first vascular tissue based on the first time-attenuation curve; determines one or more of a second contrast agent arrival time, a second peak contrast agent arrival time, or a second contrast agent mean transit time for the vascular tissue of interest based on the second time-attenuation curve; and determines one or more of a third contrast agent arrival a third time, peak contrast agent arrival time, or a third contrast agent mean transit time for the connecting vascular tissue based on the third time-attenuation curve.

7. The system of claim 6, the computer processor further determines, based on the first perfusion information, the second perfusion information and the third perfusion information, whether a perfusion deficit is in the first vascular tissue, the vascular tissue of interest, or the connecting vascular tissue.

8. The system of claim 7, wherein the perfusion deficit includes a vascular flow imbalance of contrast agent inflow into the vascular tissue of interest.

9. The system of claim 8, wherein the first vascular tissue includes right and left carotid bifurcations of the subject, the vascular tissue of interest includes right and left mid-cerebral arteries of the subject, and the connecting vascular tissue includes right and left internal carotids of the subject, and the second and third perfusion information indicates a flow imbalance indicative of a stenosis in one of the left or right internal carotids.

10. The system of claim 9, the computer processor further compares time-attenuation curves at the right and left carotid bifurcations and the right and left mid-cerebral arteries, which represents vascular flow through the right and left internal carotid arteries, and determines differences in the vascular flow in the right and left internal carotid arteries based on the comparison, wherein the differences in the vascular flow indicate the vascular flow imbalance.

11. The system of claim 10, the computer processor further deconvolves an injection pulse of known duration prior to the comparison in response to different amounts of contrast agent being injected for the pre-perfusion and the perfusion scans.

12. The system of claim 3, the computer processor further determines the first perfusion information by determining differences in vascular flow in the first vascular tissue and the vascular tissue of interest from the pre-perfusion image data and the perfusion image data.

13. The system of claim 12, the computer processor further derives the first perfusion information from an anatomical model, wherein the anatomical model structurally describes the connecting vascular tissue vascularly connecting the first vascular tissue and the vascular tissue of interest.

14. The system of claim 13, the computer processor further determines the anatomical model from computed tomography angiography image data.

15. A non-transitory computer readable storage medium containing instructions which, when executed by a computer, cause the computer to: determine contrast time-attenuation curves for pre-perfusion image data and perfusion image data from the pre-perfusion image data and the perfusion image data; derive perfusion data for a vascular tissue, which is not visible in the pre-perfusion image data and the perfusion image data but affects perfusion of tissue in the perfusion image data, based on differences in vascular flow in the tissue in the perfusion image data determined from the contrast time-attenuation curves and an anatomical model of the vascular tissue, which vascularly connects tissue in pre-perfusion image data and the tissue in the perfusion image data.

16. A method, comprising:
retrieving pre-perfusion image data acquired during a perfusion contrast enhanced pre-scan in which a scanner repeatedly scans a first vascular tissue of a subject and generates the pre-perfusion image data, which includes the first vascular tissue and does not include connecting vascular tissue, which vascularly connects the first vascular tissue of the subject and vascular tissue of interest of the subject, wherein the first vascular tissue feeds the vascular tissue of interest, which is upstream from the first vascular tissue, through the connecting vascular tissue;
determining, with a computer processor and from the pre-perfusion image data, an amount of time from an administration of a first contrast agent for the perfusion contrast enhanced pre-scan that generates the pre-perfusion image data to arrival of the administered contrast agent at the first vascular tissue;
creating, with the computer processor, an imaging plan for a perfusion scan of the vascular tissue of interest based on the amount of time so that the perfusion scan acquires data representing an arrival of an administered second contrast agent at the vascular tissue of interest;
retrieving perfusion image data generated from the perfusion scan, which is performed with the imaging plan, wherein the perfusion image data includes the vascular tissue of interest and does not include the connecting vascular tissue; and
determining, with a computer processor, first perfusion information for the connecting vascular tissue of the subject from a combination of the pre-perfusion image data, and perfusion image data.

17. The method of claim 16, further comprising:
processing the pre-perfusion image data and the perfusion image data and determining second perfusion information for the first vascular tissue from the pre-perfusion image data and third perfusion information for the vascular tissue of interest from the perfusion image data.

18. The method of claim 17, wherein the determining of the first, the second and the third perfusion information, comprises:
generating a first time-attenuation curve of contrast density for the first vascular tissue from the first perfusion image data;
generating a second time-attenuation curve of contrast density for the vascular tissue of interest from the second perfusion image data; and
deriving a third time-attenuation curve of contrast density for the connecting vascular tissue from the first time-attenuation curve and the second time-attenuation curve.

19. The method of claim 18, further including:
estimating first blood flow for the first vascular tissue based at least on the first time-attenuation curve;
estimating second blood flow for the vascular tissue of interest based at least on the second time-attenuation curve; and
deriving third blood flow for the connecting vascular tissue based on the first blood flow estimate and the second blood flow estimate.

20. The method of claim 18, further including:
determining one or more of a first contrast agent arrival time, a first peak contrast agent arrival time, or a first contrast agent mean transit time for the first vascular tissue based on the first time-attenuation curve;
determining one or more of a second contrast agent arrival time, a second peak contrast agent arrival time, or a second contrast agent mean transit time for the vascular tissue of interest based on the second time-attenuation curve; and
determining one or more of a third contrast agent arrival time, a third peak contrast agent arrival time, or a third contrast agent mean transit time for the connecting vascular tissue based on the third time-attenuation curve.

21. The method of claim 20, further including:
detecting a perfusion deficit from the perfusion image data; and
determining, based on the first perfusion information, the pre-perfusion image data and the perfusion image data, that the perfusion deficit is in the connecting vascular tissue.

22. The method of claim 21, wherein the perfusion deficit is detected as a vascular flow imbalance of contrast agent inflow into the vascular tissue of interest.

23. The method of claim 22, wherein the first vascular tissue includes right and left carotid bifurcations of the subject, the vascular tissue of interest includes right and left mid-cerebral arteries of the subject, and the connecting vascular tissue includes right and left internal carotids of the subject, and the vascular flow imbalance indicates a stenosis in one of the right or left internal carotids.

24. The method of claim 23, further comprising:
comparing time-attenuation curves for the right and left carotid bifurcations and the right and left mid-cerebral arteries, and determining differences in the vascular flow in the right and left internal carotid arteries based on the comparison, wherein the differences in the vascular flow indicates the vascular flow imbalance.

25. The method of claim 24, further comprising:
deconvolving an injection pulse of known duration prior to the comparison in response to different amounts of contrast agent being injected for the pre-perfusion and the perfusion scans.

26. The method of claim 16, further including:
determining the first perfusion information by determining differences in vascular flow in the first vascular tissue and the vascular tissue of interest from the pre-perfusion image data and the perfusion image data.

27. The method of claim 26, further including:
deriving the first perfusion information using an anatomical model, wherein the anatomical model structurally describes the connecting vascular tissue vascularly connecting the first vascular tissue and the vascular tissue of interest.

28. The method of claim 26, further including:
detecting a perfusion deficit in response to the differences indicating a vascular flow imbalance.

* * * * *